United States Patent [19]

Candussi et al.

[11] 4,396,612

[45] Aug. 2, 1983

[54] USE OF PHOSPHOLIPIDS AS MOULD INHIBITING AGENTS IN SILOED FORAGE

[75] Inventors: Francesca Candussi, Via Duca d'Aosta, Spilimbergo, (Perdenone), Italy; Giovanni Leoni, Rome; Carlo Rossi, Motta di Livenza, both of Italy

[73] Assignees: Francesca Candussi, Treviso; Agrozoolab; Lecithos Srl., both of Padua; Com. At. Im. Srl., Milan, all of Italy

[21] Appl. No.: 290,933

[22] Filed: Aug. 7, 1981

[30] Foreign Application Priority Data

Aug. 14, 1980 [IT] Italy ................. 24174 A/80

[51] Int. Cl.$^3$ .................. A23J 7/02; A01N 31/00
[52] U.S. Cl. ...................... 424/180; 260/403; 424/195; 424/199; 106/18.31

[58] Field of Search ............. 260/403; 106/18.31, 106/244; 427/180, 195, 199

[56] References Cited

U.S. PATENT DOCUMENTS

| | | | |
|---|---|---|---|
| 2,753,362 | 7/1956 | Owades et al. | 260/403 |
| 3,031,478 | 4/1962 | Klenk et al. | 260/403 |
| 3,451,826 | 6/1969 | Mulder | 260/403 |
| 3,505,074 | 4/1970 | Pardun | 260/403 |
| 3,752,832 | 8/1973 | Maruyama et al. | 260/403 |
| 4,217,346 | 8/1980 | Diana | 260/403 |

*Primary Examiner*—Thomas A. Waltz
*Attorney, Agent, or Firm*—Stevens, Davis, Miller & Mosher

[57] ABSTRACT

Compositions containing as their main ingredient phospholipids of vegetable origin, preferably from soybean oil, are used by dispersing in water and spraying on to siloed forage to prevent mould formation therein.

4 Claims, No Drawings

USE OF PHOSPHOLIPIDS AS MOULD INHIBITING AGENTS IN SILOED FORAGE

This invention relates to a new use for phospholipids, in particular phospholipids of vegetable origin, either alone or in mixture with other substances also present in the initial vegetable substances from which they are extracted. More precisely, according to the present invention, the phospholipids or the mixtures which contain them as their main component are used for preventing mould formation in siloed forage.

Green forage is chopped into a length of 4–10 mm and then preserved in deep pits where it is disposed in successive layers having a thickness of a few centimeters and compacted. It is then withdrawn from these pits during the year by cutting vertical sections.

As soon as siloing has taken place, lactic fermentation begins in the mass, and by lowering the pH of the mass makes the product sufficiently stable and preservable for the necessary period of time.

However, at the same time, those zones in which substantial air and/or condensate remain provide a very favourable habitat for moulds which besides destroying large quantities of product produce toxins and amines which transform a product considered to be an excellent and unsubstitutable food, into a product which is not only poor but also toxic. Mould formation takes place mainly in the intermediate layers wherever filling had to be suspended for any reason, and in the top part of the siloed mass which is exposed to air and which can obviously not be compressed to the same extent as the remainder, and always contains considerable quantities of air and condensate. In all cases, these moulds produce considerable product losses both in terms of quality and quantity.

Up to the present time, only propionic acid and formic acid or their salts have been used for mould control in forage. These products interfere with the metabolism of the moulds, so killing them, but have to be used in limited quantities because they give the product a taste which is unpleasant to the animals. In any case, they give only poor results. A new group of compounds, namely phospholipids, have now been discovered which either alone or in composition with other substances of vegetable origin provide a complete and satisfactory solution to the problem from all viewpoints. These compounds form the subject matter of the present invention. Phospholipids have an action mechanism which is completely different from known stabilisers in that they do not interfere with the metabolism of the moulds but instead substract oxygen from them, this being an essential element for their proliferation, which occurs only in the aerobic phase. In addition, by blocking the moulds and leaving free space for the lactic ferments, the phospholipids allow biological control of those other bacteria which have a high consumption of energy-giving substances and produce large quantities of toxic metabolites.

Finally, it should be noted that the phospholipids and the compositions which contain them are themselves products of high nutritive power, which contribute to further enriching the forage from the food aspect.

The phospholipids used according to the present invention are of vegetable origin, and are preferably extracted from soybean oil.

As previously stated, they can be used alone, but are preferably used in combination with other products also of vegetable origin which increase their effectiveness.

The preferred compounds according to the present invention comprise the following ingredients:
 phospholipids
 vegetable oils
 polyethyleneglycol esters of fatty acids
 glucosides The preferred proportions of the said ingredients are as follows:
 phospholipids: 40–60%
 vegetable oils: 30–35%
 polyethyleneglycol esters: 9–20%
 glucosides: 1–5%

A typical composition commonly used with optimum results, and obtained from soybean oil, comprises the following ingredients in the proportions indicated:
 phospholipids: 50%
  (13% phosphatidylethanolamines, acidity No. 18–22, peroxide No. <3)
 polyethyleneglycol esters of fatty acids: 15%
 D-sorbitol: 2%
 soybean oil: 33%

The compositions, which are generally brown fluids, are used as approximately 10% dispersions in water, and are applied by means of sprayers. Applications is commenced by washing the base and walls of the silo pits with the dispersion according to the invention, using a quantity of about 500 cc/m$^2$. The dispersion is then applied to the terminal surface of the siloed mass in a quantity of about 3 l/m$^2$. After evaporation of the aqueous carrier, the product forms a film which in practice isolates the siloed mass from the outside, so preventing its contact with oxygen and thus making it impossible for any aerobic mould to develop. At the same time, the film prevents any dispersion of the $CO_2$ produced by the lactic fermentation, this being highly useful for preserving the mass. If filling in the form of layers has to be suspended during siloing for any reason, the surface of the siloed material which remains temporarily exposed must be protected with the 10% suspension of phospholipids according to the invention.

The quantity applied can vary from 500 cc/m$^2$ to 3 l/m$^2$, in proportion to the time for which the filling process is suspended.

In all cases, within the range indicated, the quantity of liquid to be used also depends on the dryness of the forage mass, because the drier the mass the less it can be packed down, and the less easy it becomes to exclude the air. The phospholipid-based compositions according to the invention can be used as mould inhibiting agents for any type of siloed grasses such as siloed barley, lolium, straw, corn, wheat hayes of vegetables or of gramineous essences or mixed hayes untimely harvested and thus with a moisture content higher than that of the completely dryed hayes.

We claim:

1. A method of inhibiting mould in siloed grasses comprising applying thereto an aqueous dispersion of a composition comprising phospholipids of vegetable origin in mixture with other substances of vegetable origin selected from the group consisting of vegetable oils, polyethylene glycol esters of fatty acids and glucosides.

2. A method according to claim 1 wherein all the components are derived from soybean processing.

3. A method according to claim 1 wherein the individual ingredients are present in the following proportions:
Phospholipids: 40–60%
Vegetable oils: 30–35%
Polyethyleneglycol esters of fatty acids: 9–20%
Glucosides: 1–5%.

4. A method according to claim 1 wherein the individual ingredients are present in the following proportions:
Soybean phospholipids: 50%
Polyethyleneglycol esters of soybean oil fatty acids: 15%
Soybean oil: 33%
D-sorbitol: 2%.

* * * * *